United States Patent [19]

Mendius

[11] Patent Number: 5,741,292
[45] Date of Patent: Apr. 21, 1998

[54] PUNCTUM DILATING AND PLUG INSERTING INSTRUMENT WITH PUSH-BUTTON PLUG RELEASE

[75] Inventor: Richard Mendius, Millington, Tenn.

[73] Assignee: Eagle Vision, Memphis, Tenn.

[21] Appl. No.: 843,127

[22] Filed: Apr. 28, 1997

Related U.S. Application Data

[63] Continuation of Ser. No. 548,480, Oct. 26, 1995, abandoned.

[51] Int. Cl.$^6$ ................................................ A61B 17/00
[52] U.S. Cl. .............................. 606/191; 606/1; 128/831
[58] Field of Search ...................................... 606/107, 108, 606/109, 140, 141, 170, 205, 174, 191, 1; 128/831

[56] References Cited

U.S. PATENT DOCUMENTS

| | | | |
|---|---|---|---|
| 3,897,786 | 8/1975 | Garnett et al. | 606/109 |
| 4,258,716 | 3/1981 | Sutherland | 606/174 X |
| 4,267,839 | 5/1981 | Laufe et al. | 606/141 |
| 4,760,848 | 8/1988 | Hasson | 606/174 X |
| 5,122,149 | 6/1992 | Broome | 606/140 |
| 5,282,817 | 2/1994 | Hoogeboom et al. | 606/174 X |
| 5,355,871 | 10/1994 | Hurley et al. | 606/170 |
| 5,634,918 | 6/1997 | Richards | 606/205 X |

OTHER PUBLICATIONS

GWB International, Ltd. brochure and instructions for FCI Punctum Dilator & Plug Inserter.
Lacrimedics, Inc. brochure for Lacrimal Plug™ with inserter.
Eagle Vision, Inc. brochure for Michalos Insertion Forceps.

*Primary Examiner*—Michael H. Thaler
*Attorney, Agent, or Firm*—Jack Lo

[57] ABSTRACT

A punctum dilating and plug inserting instrument includes a cylindrical body with a first end being a plug inserting tip, and a second end being a punctum dilating tip. An elongated button is arranged longitudinally along the body. The button includes a fixed end and a slidable end; the fixed end being positioned between the slidable end and the plug inserting tip. The button also includes an outwardly bowing inner surface spaced from the body. A wire is slidably positioned longitudinally within the body. The wire includes an outer end protruding from the plug inserting tip, and an inner end attached to the slidable end of the button. A conventional punctum plug is attached to the outer end of the wire, and can be inserted into a punctum after the punctum is dilated by the dilating tip. The plug is released by depressing the button, which causes the outwardly bowing inner surface to be moved inwardly against the body, and the slidable end to be moved along the body away from the fixed end and the plug inserting tip. The wire is thus pulled by the slidable end of the button away from the punctum plug to release it.

5 Claims, 3 Drawing Sheets

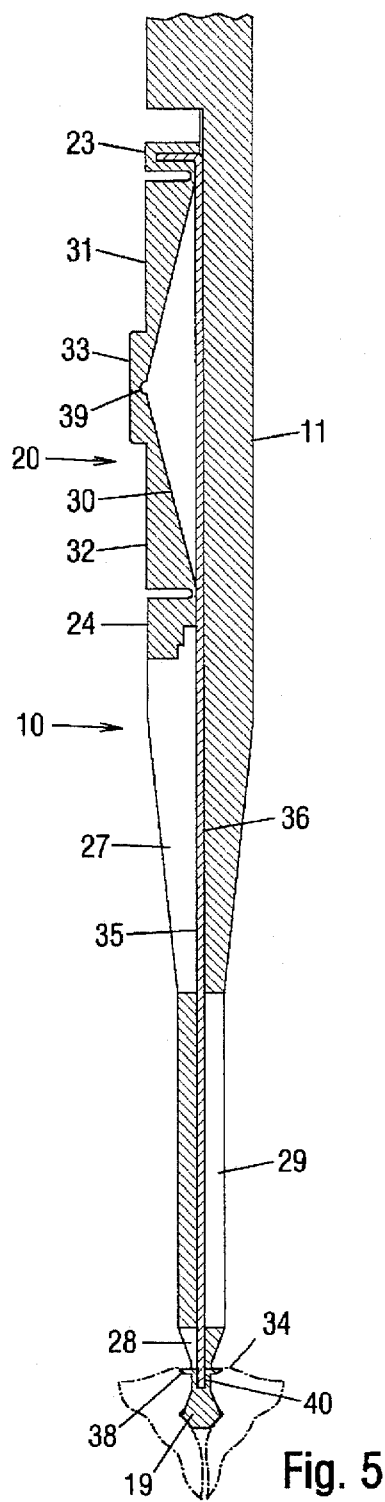
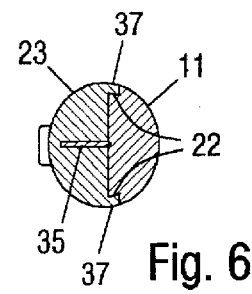
Fig. 6
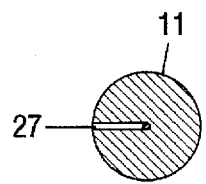
Fig. 7
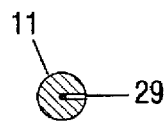
Fig. 8
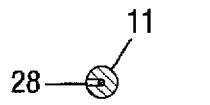
Fig. 9
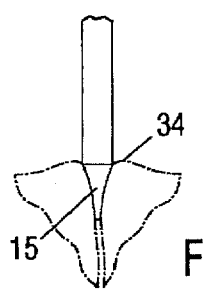
Fig. 4
Fig. 5

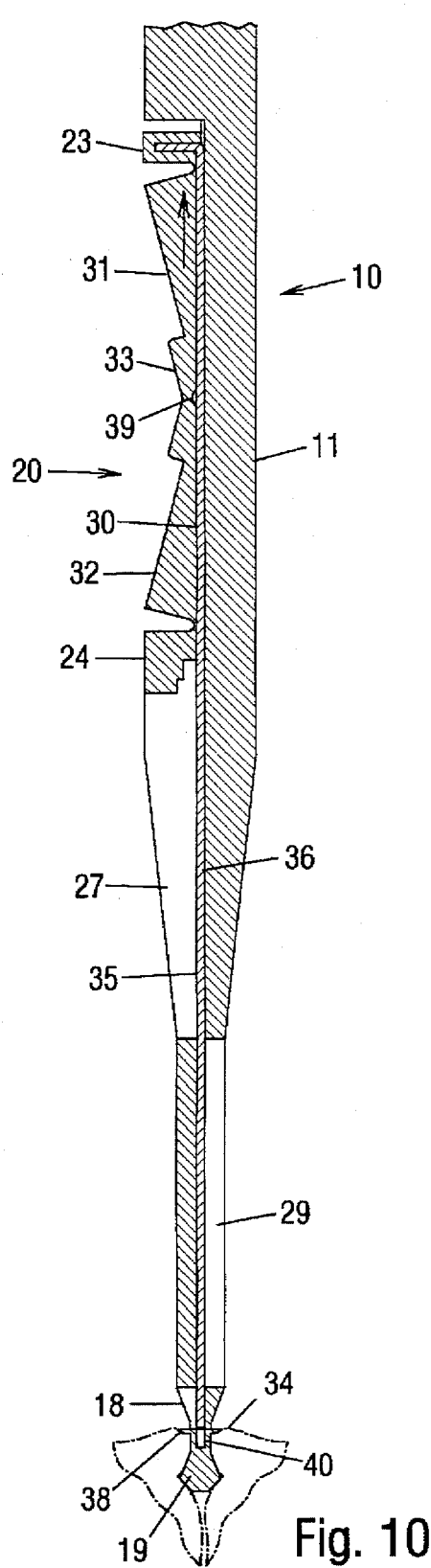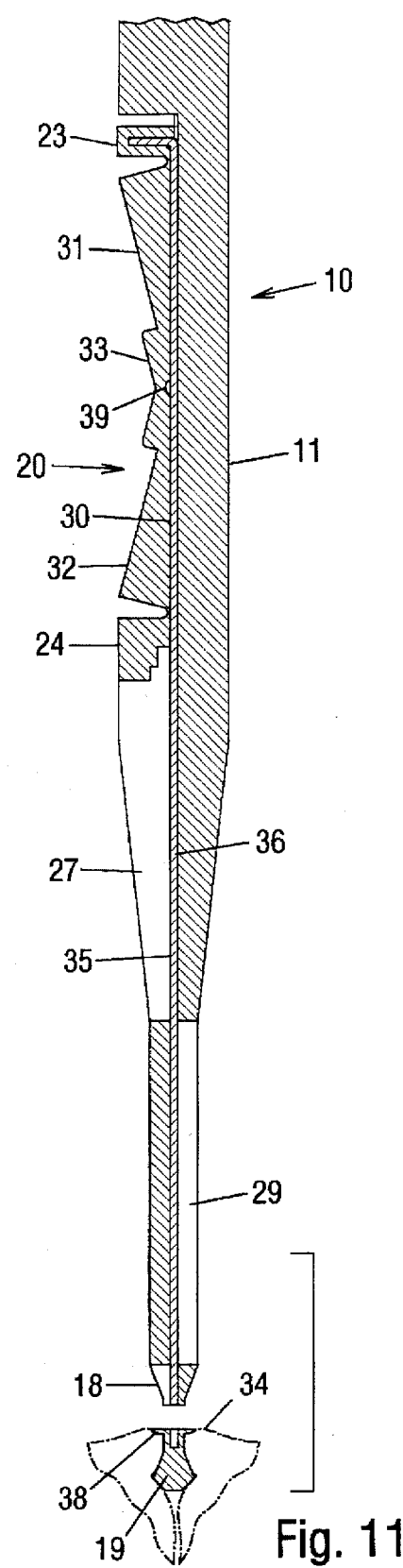

PUNCTUM DILATING AND PLUG INSERTING INSTRUMENT WITH PUSH-BUTTON PLUG RELEASE

This application is a continuation of prior application Ser. No. 08/548,480, filed on Oct. 26, 1995, now abandoned.

BACKGROUND OF THE INVENTION

1. Field Of The Invention

This invention relates generally to punctum plug insertion instruments, specifically to an instrument for dilating a punctum and inserting a punctum plug, and which provides push-button release of the plug.

2. Prior Art

The surface of the eye and the inner surface of the eyelid are moisturized by tears constantly produced by glands around the eye. A tiny hole, known as the lacrimal punctum, at the inner corner of each upper and lower lid margin drains the tears away through ducts for proper circulation.

Contact lens wearers who suffer from dry eye, or insufficient tear production, experience a great deal of discomfort because of insufficient lubrication between the lens and the surface of the eye. One solution is to occlude or block the punctum to prevent tear drainage. Permanent punctal occlusion can be performed surgically, whereas temporary occlusion can be performed by inserting a tiny plug in the punctum. A typical punctum plug includes a cylindrical or conical body, and a coaxial hole for being attached to the tip of an insertion instrument.

A variety of instruments are available for inserting punctum plugs. Lacrimedics, Inc. of Rialto, Calif., sells a punctum plug preloaded on the tip of a pin stuck into a piece of foam. The pin is used to push the plug into a punctum. After the plug is properly seated, the pin is withdrawn. However, the pin must be precisely held to position the plug in a neutral position during withdrawal, i.e., it must not be canted to one side. Such precision is difficult to achieve, so that the pin often sticks to the plug enough to unseat it during withdrawal.

Another plug insertion instrument is sold under the trademark "Michalos Insertion Forceps" by Eagle Vision, Inc. of Memphis, Tenn. It includes a pin arranged at one tip for attaching to a plug, and a gripping hook arranged on the other tip for gripping and securing the plug prior to insertion. After the plug is inserted into a punctum, the gripping hook is released, so that the pin can be withdrawn from the plug. Again, the pin may stick to the plug, so that when the pin is withdrawn, the plug may be unseated. Furthermore, a separate instrument is required for dilating the punctum prior to plug insertion.

A punctum inserter sold by GWB International, Ltd. provides a mechanism for releasing the plug after insertion. It includes a main cylindrical body, and a central wire extending coaxially from one end thereof. A tube is slidably positioned around the central wire. An elliptical spring has one end attached to the main body and another end attached to the slidable tube. A punctum plug is attached to the tip of the central wire before use. A thin rod with a pointed end extends from another end of the main body for dilating a punctum prior to plug insertion. When the punctum is properly dilated, the plug is inserted thereinto, and the spring is squeezed, which elongates in a longitudinal direction, and slides the tube forwardly to dislodge the plug from the tip of the central wire. However, the elliptical spring makes a poor handle that is awkward to hold and difficult to control. Furthermore, when the slidable tube is activated to dislodge the plug, it tends to push the plug deeper into the punctum than desired.

OBJECTS OF THE INVENTION

Accordingly the primary object of the present invention is to provide a punctum dilating and plug inserting instrument that is shaped for precise handling.

Another object of the present invention is to provide a punctum dilating and plug inserting instrument that is usable for dilating a punctum prior to plug insertion.

Another object of the present invention is to provide a punctum dilating and plug inserting instrument that is usable for inserting a punctum plug into a punctum.

Yet another object of the present invention is to provide a punctum dilating and plug inserting instrument that reliably and smoothly releases the plug after insertion without disturbing the plug's position.

Still another object of the present invention is to provide a punctum dilating and plug inserting instrument that is very economical to manufacture, so that it is disposable after a single use.

Other objects of the present invention will become apparent from a study of the following description and the accompanying drawings.

SUMMARY OF THE INVENTION

A punctum dilating and plug inserting instrument includes an elongated cylindrical body, and a wire slidably positioned longitudinally therein. A conventional punctum plug is preloaded on an outer end of the wire protruding from one end of the body. An elongated button is positioned longitudinally along the body, and has an outwardly bowing inner surface spaced from the body. The button also has a fixed end and a slidable end; the fixed end being positioned between the slidable end and the plug. The wire has an inner end attached to the slidable end of the button. A tapered dilating tip is attached to the body for dilating a punctum prior to plug insertion. After the plug is inserted, it is released by depressing the button, which is collapsed against the body and lengthened in a longitudinal direction. The slidable end of the button is therefore moved away from the fixed end, and the wire is pulled by the slidable end away from the plug to release it.

BRIEF DESCRIPTION OF THE DRAWINGS

FIG. 4 is a side view of a dilating tip of the instrument dilating a punctum.

FIG. 5 is a side sectional view of the instrument taken along line 5—5 in FIG. 1.

FIG. 6 is an end sectional view of the instrument taken along line 6—6 in FIG. 3.

FIG. 7 is an end sectional view of the instrument taken along line 7—7 in FIG. 3.

FIG. 8 is an end sectional view of the instrument taken along line 8—8 in FIG. 3.

FIG. 9 is an end sectional view of the instrument taken along line 9—9 in FIG. 3.

FIG. 10 is a side sectional view of the instrument after a punctum plug is released.

FIG. 11 is a side sectional view of the instrument being moved away from the plug.

Drawing Reference Numerals

| | |
|---|---|
| 10. Instrument | 11. Cylindrical Body |
| 12. Larger Diameter Part Of Body | 13. Larger Diameter Part Of Body |
| 14. Rod | 15. Second End |
| 16. Rod | 17. Tapered Shoulder |
| 18. First End | 19. Punctum Plug |
| 20. Button | 21. Recess |
| 22. Rails | 23. Slidable End Of Button |
| 24. Fixed End Of Button | 25. Key |
| 26. Locking Slot | 27. Slot |
| 28. Slot | 29. Slot |
| 30. Inner Surface Of Button | 31. Portion Of Button |
| 32. Portion Of Button | 33. Breakable Bridge |
| 34. Punctum | 35. Wire |
| 36. Channel | 37. Ears |
| 38. Flange | 39. Notch |
| 40. Mounting Hole | |

DESCRIPTION—FIG. 1

Figure 1:
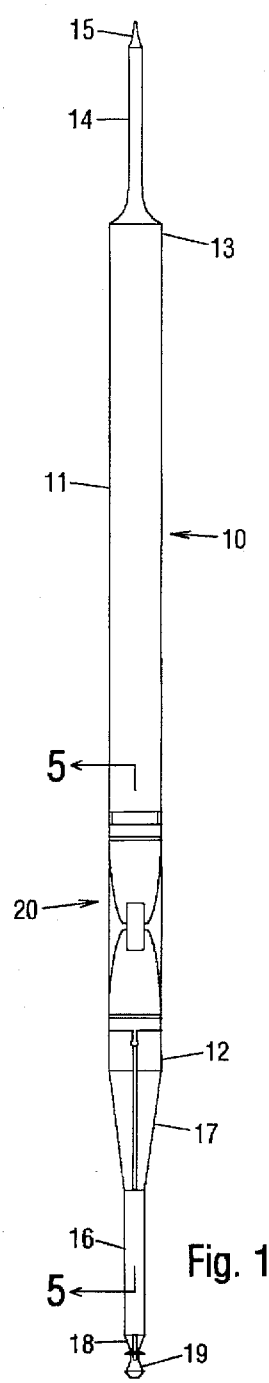
FIG. 1 is a front view of a punctum dilating and plug inserting instrument in accordance with a preferred embodiment of the invention.

In accordance with a preferred embodiment of the invention shown in the front view in FIG. 1, a punctum dilating and plug inserting instrument 10 includes an elongated cylindrical body 11 with a first end 18 being a plug inserting tip, and a second end 15 being a tapered and radiused punctum dilating tip. A narrower rod 14 forms a transition between second end 15 and a larger diameter part 13 of body 11. Another narrower rod 16 and a tapered shoulder 17 form a transition between first end 18 and a larger diameter part 12 of body 11. A conventional, very soft punctum plug 19 is attached to first end 18; the method of attachment is disclosed in conjunction with FIG. 5. Body 11 is about the size and shape of a pencil, which makes it very easy to handle and precisely controllable.

DESCRIPTION—FIG. 2

Figure 2:
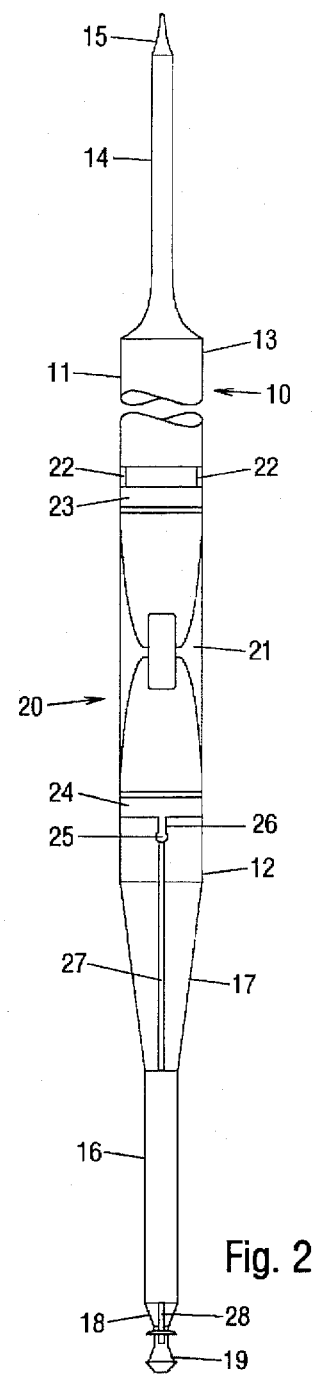
FIG. 2 is an enlarged front view of the instrument.

As shown in an enlarged from view of instrument 10 in FIG. 2, a button 20 elongated along the axis of body 11 is positioned in a recess 21 arranged near first end 18. A pair of rails 22 are arranged partially along the sides of recess 21. Button 20 includes a slidable end 23 and a fixed end 24; fixed end 24 is positioned between slidable end 23 and first end 18. Fixed end 24 is held in place by a key 25 extending therefrom and fitted into a locking slot 26 on body 11. Slots 27 and 28 are arranged on body 11. Knurls (not shown) are also provided on body 11 and button 20 for traction.

DESCRIPTION—FIG. 3

Figure 3:
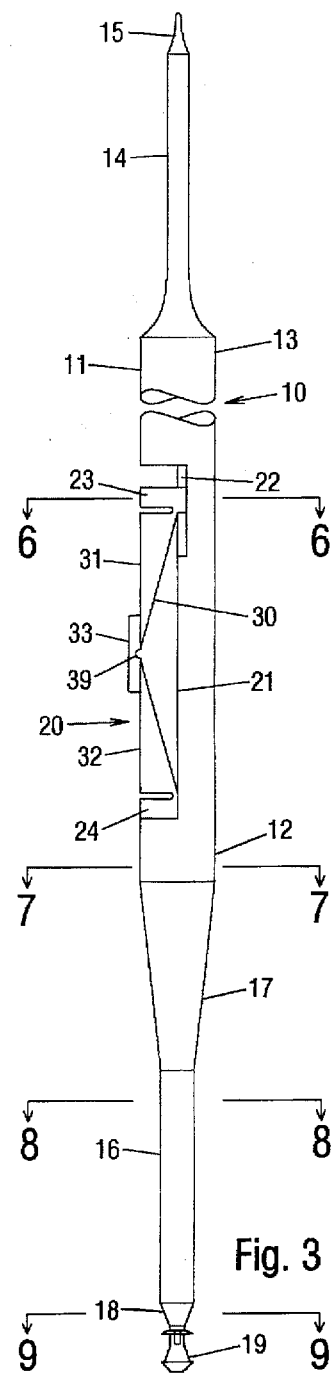
FIG. 3 is an enlarged side view of the instrument.

As shown in an enlarged side view of instrument 10 in FIG. 3, button 20 includes an outwardly bowing inner surface 30, which is formed by the straight inner sides of portions 31 and 32 that define an obtuse angle. A breakable bridge 33, which has a notch 39 on an inner side thereof, is positioned at an apex of outwardly bowing inner surface 30. Slidable end 23 and fixed end 24 are pivotably connected to portions 31 and 32, respectively, adjacent inner surface 30.

DESCRIPTION—FIG. 4

Prior to plug insertion, second end or dilating tip 15 is lubricated with a suitable lubricant (not shown), such as artificial tear, and inserted into a punctum 34 to dilate it.

DESCRIPTION—FIGS. 5–9

As shown in the side sectional view in FIG. 5, a wire 35 is slidably and coaxially positioned within body 11. The outer end of wire 35 is frictionally fitted into a mounting hole 40 of plug 19. The inner end of wire 35 is bent at a right angle and anchored within slidable end 23 of button 20. A channel 36 for wire 35 is formed by slots 27–29, which alternately extend into body 11 slightly past the axis thereof from opposite directions, as further illustrated by the end sectional views in FIGS. 7–9. Slots 27–29 allow channel 36 to be formed in body 11 with inexpensive two-part molds.

As shown in FIG. 6, slidable end 23 is secured to body 11 by a pair of inwardly angled ears 37 that grip inwardly angled rails 22.

When punctum 34 is properly dilated, plug 19 is lubricated with a suitable lubricant (not shown), such as artificial tear, and inserted into punctum 34 by pushing and twisting cylindrical body 11 about its longitudinal axis. Plug 19 is inserted deep enough so that the top of its soft flange 38 is slightly distorted to fit flush with the rim of punctum 34.

DESCRIPTION—FIGS. 10 and 11

As shown in FIG. 10, after plug 19 is properly seated, it is released by simply holding instrument 10 steady, and depressing the middle of button 20 against body 11. When a moderate force is applied, bridge 33 is snapped at notch 39. Button 20 is thus collapsed inwardly and inner surface 30 is straightened, so that slidable end 23 is slid along body 11 away from fixed end 24, as indicated by the arrow, and pull wire 35 away from plug 19. During the withdrawal of wire 35, first end 18 of body 11 remains butted against plug 19, so that plug 19 is prevented from being unseated. After plug release, instrument 10 can be moved away and disposed of, as shown in FIG. 11.

SUMMARY, RAMIFICATIONS, AND SCOPE

Accordingly, I have provided a punctum dilating and plug inserting instrument that is shaped for easy and precise handling. It can be used to dilate a punctum to prepare it for plug insertion. It can be used to insert and position a punctum plug into a punctum. It is easily controllable to release the plug without disturbing the plug's position. It is economical to manufacture, so that it is disposable after a single use.

Although the above descriptions are specific, they should not be considered as limitations on the scope of the invention, but only as examples of the embodiments. Many other ramifications and variations are possible within the teachings of the invention. For example, button 20 can be made of a resilient material, so that instead of snapping, it rebounds into shape when released, which allows the instrument to be reloaded with another plug and reused. The instrument can be used for inserting and releasing other objects or devices. Therefore, the scope of the invention should be determined by the appended claims and their legal equivalents, not by the examples given.

I claim:

1. A combination of a punctum plug and an instrument for retaining and releasing said punctum plug, comprising:

an elongated body having a forward end and a rear end, said elongated body having a recess extending longitudinally thereon;

a punctum plug positioned against said forward end of said body;

an elongated button positioned within said recess and flush with an outer surface of said elongated body, said button having a fixed end fixedly attached to said elongated body at one end of said recess and a slidable end slidable along said recess, said fixed end being positioned between said slidable end and said forward end of said body, said button having an outwardly bowing inner surface spaced from a bottom surface of said recess, so that when said button is depressed, said outwardly bowing inner surface is moved inwardly against said bottom surface of said recess, and said slidable end is moved longitudinally along said body away from said fixed end; and a wire slidably positioned longitudinally along said body, said wire having an outer end extending from said forward end of said body and frictionally fitted in a mounting hole in said punctum plug, said wire having an inner end fixedly attached to said slidable end of said button, so that before said button is depressed, said punctum plug is retained against said forward end of said body by said wire, and when said button is depressed, said wire is pulled by said slidable end of said button away from said mounting hole of said punctum plug to release said punctum plug from said instrument.

2. The instrument of claim 1 wherein said elongated body is cylindrical.

3. The instrument of claim 1 wherein said outwardly bowing inner surface of said button comprises two straight surfaces defining an obtuse angle, each of said straight surfaces defining an acute angle with said recess.

4. The instrument of claim 1, further including a breakable bridge arranged at an apex of said outwardly bowing inner surface.

5. The instrument of claim 1, further including a tapered dilating tip attached to said second end of said body for dilating a punctum.

* * * * *